United States Patent [19]

Kawaguchi et al.

[11] Patent Number: 4,918,136
[45] Date of Patent: Apr. 17, 1990

[54] ADHESIVE COMPOSITION

[75] Inventors: Toshio Kawaguchi, Fujisawa; Shigeri Shibuya, Sagamihara; Koshi Kusumoto, Kamakura, all of Japan

[73] Assignee: Tokuyama Soda Kabushiki Kaisha, Yamaguchi, Japan

[21] Appl. No.: 327,021

[22] Filed: Mar. 22, 1989

[51] Int. Cl.$^4$ ............................................. C08K 5/15
[52] U.S. Cl. ............................ 524/751; 523/116; 523/118; 526/268; 526/318; 526/318.2; 526/318.41; 526/318.5; 526/320; 526/326
[58] Field of Search ............... 523/116, 118, 115; 524/751, 111; 526/318, 318.2, 318.41, 318.5, 320, 326, 268

[56] References Cited

U.S. PATENT DOCUMENTS

| | | | |
|---|---|---|---|
| 4,148,988 | 4/1979 | Masuhara et al. | 526/318 |
| 4,182,035 | 1/1980 | Yamauchi et al. | 433/228 |
| 4,499,251 | 2/1985 | Omura et al. | 526/278 |
| 4,525,493 | 6/1985 | Omura et al. | 523/116 |
| 4,537,940 | 8/1985 | Omura et al. | 526/278 |
| 4,539,382 | 9/1985 | Omura et al. | 526/276 |
| 4,650,847 | 3/1987 | Omura et al. | 526/376 |

FOREIGN PATENT DOCUMENTS

| | | | |
|---|---|---|---|
| 2818068 | 11/1978 | Fed. Rep. of Germany | 523/118 |
| 57-75907 | 5/1982 | Japan | 523/118 |

Primary Examiner—Joseph L. Schofer
Assistant Examiner—R. H. Delmendo
Attorney, Agent, or Firm—Sherman and Shalloway

[57] ABSTRACT

Disclosed is an adhesive composition comprising (a) 100 parts by weight of a monomer mixture comprising a vinyl monomer having an acidic group in the molecule and a vinyl monomer copolymerizable with said vinyl monomer, (b) 10 to 500 parts by weight of a filler, (c) 0.01 to 10 parts by weight of a polymerization initiator and (d) 0.01 to 10 parts by weight of ascorbic acid or a derivative thereof.

This adhesive composition has a high bonding force and an excellent durability even in a severe environment, for example, in the environment in the oral cavity. Accordingly, this adhesive composition is especially valuable used as a dental adhesive.

15 Claims, No Drawings

ADHESIVE COMPOSITION

BACKGROUND OF THE INVENTION (1) Field of the Invention

The present invention relates to an adhesive composition having a high bonding force and an excellent durability. More particularly, the present invention relates to an adhesive composition especially valuable as a dental adhesive.

(2) Description of the Related Art

A variety of adhesive are used in various fields, and recently, they are extensively used in the automobile industry, the electric power industry and related industries, the construction field and the medical industry. Adhesives having excellent properties required in the respective fields have been developed. Adhesives used in the medical field, for example, dental adhesives used for restoration of teeth, are required to have strong bonding force and high durability sufficient to resist severe conditions such as those in the oral cavity. Accordingly, various dental adhesives having special functions capable of resisting severe conditions have been proposed.

For example, Japanese Pat. No. 33363/81 proposes an adhesive composition comprising an acrylic acid ester type vinyl monomer, an organic peroxide, and amine and a sulfinic acid salt. In this adhesive composition, it is intended to increase the bonding strength by using a ternary curing system comprising an organic peroxide, an amine and a sulfinic acid salt. Indeed, according to this proposal, a certain improvement over the conventional adhesive compositions can be attained. However, the adhesiveness to the dentine of a tooth is still insufficient, and it is necessary that the bonding force to the enamel of a tooth or a metal should be increased.

Japanese Patent Publication No. 36791/79 proposes a dental adhesive composition comprising an acrylic acid ester type vinyl monomer, an organic peroxide, an amine and an L-ascorbic acid. The object of this proposal is to adjust the curing time of the dental adhesive composition, and it is taught that this composition is advantageous in that an appropriate operation time can be obtained by using an L-ascorbic acid as the co-catalyst. However, from the results of tracing experiments made by us, it was confirmed that increase of the bonding force cannot be expected, though the curing time can be effectively adjusted.

Furthermore, Japanese Patent Publication No. 17513/83 and Japanese Patent Publication No. 30681/84 propose an adhesive comprising an acid group-containing monomer such as 4-methacryloxyethyltrimellitic acid and/or an anhydride thereof, a vinyl compound and a radical initiator. In this adhesive composition, if tri-n-butylborane oxide is used as a catalyst, the bonding force to the dentine of a tooth can be improved, but since tri-n-butylborane oxide reacts with oxygen in air and ignition is caused or the oxide is rendered inactive, scrupulous care is necessary for the handling. Moreover, the improvement of the adhesion strength is still insufficient.

Therefore, development of an adhesive composition having sufficient bonding force and durability even in a special environment, for example, a dental adhesive having such excellent characteristics in the oral cavity, is eagerly desired in the art.

SUMMARY OF THE INVENTION

It is therefore a primary object of the present invention to provide an adhesive composition having strong bonding force and high durability in various fields, which is especially valuable as a dental adhesive.

Another object of the present invention is to provide an adhesive composition having a high adhesion strength to the dentine of a tooth.

Other objects of the present invention will become apparent from the detailed description given hereinafter.

The present invention is to provide a novel adhesive composition which has high adhesion strength and excellent durability even in a severe environment such as the environment in the oral cavity.

More specifically, in accordance with the present invention, there is provided an adhesive composition comprising (a) 100 parts by weight of a monomer mixture comprising a vinyl monomer having an acidic group in the molecule and a vinyl monomer copolymerizable with said vinyl monomer, (b) 10 to 500 parts by weight of a filler, (c) 0.01 to 10 parts by weight of a polymerization initiator and (d) 0.01 to 10 parts by weight of ascorbic acid or a derivative thereof.

DETAILED DESCRIPTION OF THE PREFERRED EMBODIMENTS

One constituent component of the adhesive composition of the present invention is a monomer mixture comprising a vinyl monomer having an acidic group in the molecule (hereinafter referred to as "acidic group-containing monomer") and a vinyl monomer copolymerizable with said acidic group-containing monomer.

The acidic group-containing vinyl monomer is a component indispensable for maintaining the adhesive strength of the adhesive composition of the present invention at a very high level. However, if the acidic group-containing monomer alone is used as the monomer component, the viscosity of the adhesive composition is too high and the operation adaptability is poor, and the practical handling becomes difficult. Accordingly, in the present invention, the operation adaptability is improved by using a vinyl monomer copolymerizable with the acidic group-containing vinyl monomer. Therefore, the composition of the monomer mixture is mainly influenced by the properties of the acidic group-containing vinyl monomer. It is sufficient if the content of the acidic group-containing vinyl monomer in the monomer mixture is 1 to 90% by weight, preferably 1 to 50% by weight.

A vinyl monomer having an acidic functional group in the molecule can be used as the acidic group-containing monomer without any limitation in the present invention. For example, vinyl monomers having a functional group such as a carboxylic acid, phosphoric acid or sulfonic acid group and a polymerizable unsaturated group are preferably used. As specific examples of the acidic group-containing vinyl monomer, there can be mentioned carboxylic acid group-containing vinyl monomers such as methacrylic acid, acrylic acid, 2-acryloxypropionic acid, p-methacryloxybenzoic acid, 4-methacryloxyethyltrimellitic acid, its anhydride, 4-vinylbenzoic acid, 7-methacryloxy-1,1-heptane-dicarboxylic acid, 11-methacryloxy-1,1-undecane-dicarboxylic acid and 13-methacryloxy-1,1-tridecane-dicarboxylic acid, phosphoric acid group-containing vinyl monomers such as vinylphosphoric acid, 2-methacryloxyethyl phosphate, 2-methacryloyloxyethyl phosphate, 2-methacryloyloxyethylphenyl hydrogenphosphate, 10-methacryloxydecyl phosphate and a reaction product between bisphenol A diglycidyl methacrylate and phosphrous oxychloride, and sulfonic acid group-containing monomers such as vinylsulfonic acid, 2-sulfoethyl methacrylic acid, vinylbenzylsulfonic acid and methacryloxydecyl 5-sulfo-salicylate.

In order to obtain an adhesive composition having an especially high adhesiveness, it is preferred that an acidic group-containing acrylate or methacrylate type vinyl monomer having an alkyl or aryl group having 4 to 12 carbon atoms be used as the acidic group-containing vinyl monomer. A vinyl monomer having a structure in which a carboxylic acid group or its anhydride group is directly bonded to the alkyl or aryl group is especially preferred. These acidic group-containing vinyl monomers can be represented by the following general formula (I) or (II)

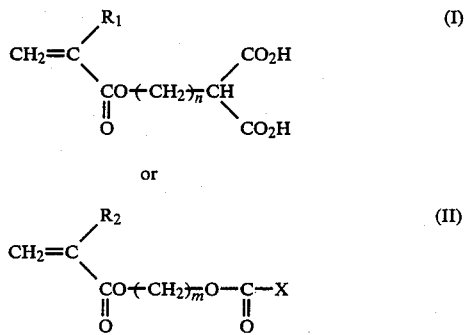

wherein $R_1$ stands for a hydrogen atom or a methyl group, n is a number of from 4 to 12, $R_2$ stands for a hydrogen atom or a methyl group, m is a number of from 2 to 4, and X is

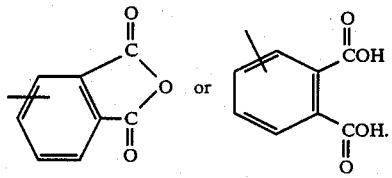

As the acidic group-containing vinyl monomer represented by the general formula (I), there can be mentioned 7-methacryloxy-1,1-heptane-dicarboxylic acid, 11-methacryloxy-1,1-undecane-dicarboxylic acid and 13-methacryloxy-1,1-tridecane-dicarboxylic acid. As the acidic group-containing vinyl monomer represented by the general formula (II), there can be mentioned 4-methacryloxyethyltrimellitic acid and its anhydride.

By using the vinyl monomer represented by the general formula (I) or (II), not only the adhesiveness but also the water resistance can be improved in the obtained adhesive composition.

An acidic group-free vinyl monomer copolymerizable with the acidic group-containing vinyl monomer can be used as the vinyl monomer to be mixed with the acidic group-containing monomer without any limitation. Acrylic acid esters and methacrylic acid esters are preferably used.

As specific examples of the copolymerizable vinyl monomer preferably used in the present invention, there can be mentioned monofunctional vinyl monomers such as methyl acrylate, methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, n-hexyl acrylate, n-hexyl methacrylate, 2-ethylhexyl acrylate, 2-ethylhexyl methacrylate, tridecyl acrylate, tridecyl methacrylate, stearyl acrylate, stearyl methacrylate, 2-hydroxyethyl acrylate, 2-hydroxyethyl methacrylate, 2-hydroxylpropyl acrylate, 2-hydroxypropyl methacrylate, glycidyl acrylate, glycidyl methacrylate, methoxydiethylene glycol acrylate and methoxydiethylene glycol methacrylate, and polyfunctional vinyl monomers such as ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, propylene glycol diacrylate, propylene glycol dimethacrylate, 1,4-butane-diol diacrylate, 1,4-butane-diol dimethacrylate, 1,6-hexane-diol diacrylate, 1,6-hexane-diol dimethacrylate, neopentyl glycol diacrylate, neopentyl glycol dimethacrylate, 1,10-decane-diol diacrylate, 1,10-decane-diol dimethacrylate, bisphenol A diacrylate, bisphenol A dimethacrylate, 2,2'-bis-[acryloyloxypolyethoxyphenyl]propane, 2,2'-bis-[methacryloyloxypolyepoxyphenyl]propane, bisphenol A diglycidyl methacrylate, trimethylolpropane acrylate, trimethylolpropane methacrylate, trimethylolethane triacrylate, trimethylolethane trimethacrylate, tetramethylolmethane tetra-acrylate and tetramethlolmethane tetramethacrylate.

The second component (b) used in the present invention is a filler. The adhesion strength of the adhesive composition of the present invention is greatly influenced by the combination of the above-mentioned acidic group-containing vinyl monomer and ascorbic acid described hereinafter. However, the filler is practically important for further improving the adhesion strength. The functional mechanism of enhancing the adhesion strength by incorporation of the filler has not been elucidated, but if the filler is incorporated, the adhesion strength is at least two times as high as the adhesion strength attained when the filler is not incorporated.

The kind of the filler used in the present invention is not particularly critical. Known fillers can be used. In general, organic fillers and inorganic fillers customarily used for dental resin materials can be used singly or in combination. As the organic filler, there are preferably used homopolymers and copolymers of acrylic acid esters and methacrylic acid esters, polyvinyl chloride, polystyrene, polyesters and nylons. As the inorganic filler, there are preferably used quartz, amorphous silica, silica-zirconia, silica-titania, clay, aluminum oxide, talc, mica, kaolin, glass, barium sulfate, zirconium oxide, titanium oxide, silicon nitride, aluminum nitride, titanium nitride, silicon carbide, boron carbide, calcium carbonate, hydroxyapatite and calcium phosphate. It is generally preferred that an inorganic filler be used after it has been treated with a silane coupling agent such as γ-methacryloyloxypropyltrimetoxysilane and vinyltriethoxysilane.

In the present invention, the amount used of the filler is changed according to the kind of the filler per se and the kinds and amounts of other constituents, and the amount of the filler cannot be simply defined. However, it is generally preferred that the filler be used in an amount of 10 to 500 parts by weight per 100 parts by weight of the monomer mixture. The particle size of the filler is preferably 0.01 to 500 μm, especially preferably 0.01 to 200 μm. In the present invention, a polymer of an acrylic acid ester or methacrylic acid ester is preferably used as the filler.

The third component (c) used in the present invention is a polymerization initiator. In general, known polymerization initiators can be used singly or in combination without any limitation. In general, organic peroxides, tertiary amines and α-diketones are preferably used as the polymerization initiator. In order to improve the adhesiveness to a metal, it is especially preferred that an organic peroxide and a tertiary amine be used in combination. In order to improve the adhesiveness to resin, it is especially preferred that α-diketone and an organic peroxide be used in combination.

As preferred examples of the organic peroxide as the polymerization initiator, there can be mentioned diacyl peroxides such as dibenzoyl peroxide, 2,4-dichlorobenzoyl peroxide, dilauroyl peroxide, dioctanoyl peroxide and decanoyl peroxide, hydroperoxides such as cumene hydroperoxide and t-butyl hydroperoxide, and ketone peroxides such as cyclohexanone peroxide and methylethylketone peroxide. These organic peroxides can be used singly or in the form of a mixture of two or more of them.

As preferred examples of the tertiary amine as the polymerization initiator, there can be mentioned toluidine derivatives such as N,N-dimethyl-p-toluidine and N,N-dihydroxy-ethyl-p-toluidine, aminobenzoic acid derivatives such as 4-(N,N-diethylamino)benzoic acid, ethyl 4-(N,N-dimethylamino)-benzoate and isoamyl 4-(N,N-dimethylamino)benzoate, aminobenzaldehyde derivatives such as 4-(N,N-dimethylamino)benzaldehyde, 4-(N,N-diethylamino)benzaldehyde and 4-(methylhexylamino)-benzaldehyde, anisidine derivatives such as N,N-dimethyl-m-anisidine, N,N-dimethyl-p-anisidine and N,N-diethyl-p-anisidine, aminophenol derivatives such as N,N-dimethyl-m-aminophenol and N,N-diethyl-m-aminophenol, and aniline derivatives such as p-propoxy-N,N-dimethylaniline, p-butoxy-N,N-dimethylaniline and p-hexyloxy-N,N-dimethylaniline.

As preferred examples of α-diketone as the polymerization initiator, there can be mentioned diacetyl, 2,3-pentadione, 2,3-hexadione, benzil, 4,4'-dimethoxybenzil, 4,4'-diethoxybenzil, α-naphthyl β-naphthyl and camphorquinone.

Acyl peroxides such as dibenzoyl peroxide are especially preferred as the organic peroxide. When the tertiary amine is used in combination with an organic peroxide, toluidine derivatives such as N,N-dimethyl-p-toluidine and aminobenzoic acid derivatives such as ethyl 4-(N,N-dimethylamino)benzoate are especially preferred. When the tertiary amine is not used in combination with the organic peroxide but is used singly, an aminobenzoic acid derivative is especially preferred in view of the adhesiveness and storage stability.

In the present invention, the organic peroxide, the tertiary amine or the α-diketone is used in an amount of 0.01 to 10 parts by weight, preferably 0.05 to 5 parts by weight, per 100 parts by weight of the vinyl monomer mixture. When the organic peroxide alone is used, the amount of the organic peroxide is preferably 0.01 to 5 parts by weight, especially preferably 0.05 to 5 parts by weight, and when the tertiary amine alone is used, the amount of the tertiary amine is preferably 0.01 to 5 parts by weight, especially preferably 0.05 to 5 parts by weight. When the α-diketone alone is used, the amount of the α-diketone is preferably 0.01 to 5 parts by weight, especially preferably 0.05 to 5 parts by weight. If both of the organic peroxide and the tertiary amine are used in combination, it is preferred that the total amount be 0.01 to 5 parts by weight, especially 0.05 to 5 parts by weight, per 100 parts by weight of the vinyl monomer mixture and the organic peroxide/tertiary amine weight ratio be in the range of from 0.05 to 20. If both of the α-diketone and the organic peroxide are used in combination, it is preferred that the total amount be 0.01 to 5 parts by weight, especially 0.05 to 5 parts by weight, per 100 parts by weight of the vinyl monomer mixture and the α-diketone/organic peroxide ratio be in the range of from 0.05 to 20.

The fourth component (d) used in the present invention is ascorbic acid or a derivative thereof. As pointed out hereinbefore, an adhesive composition in which ascorbic acid or a derivative thereof is used in combination with monomers and polymerization initiator different from those used in the present invention is known. However, in the conventional adhesive composition, ascorbic acid or its derivative is used as the co-catalyst. An adhesive composition in which ascorbic acid or its derivative is used for improving the adhesive strength has not been known. In fact, in the conventional adhesive composition comprising ascorbic acid or its derivative, the adhesion strength to the dentine is 20 to 50 kg/cm$^2$ at highest. In contrast, in the adhesive composition of the present invention, the adhesion strength to the dentine is ordinarilly 90 to 100 kg/cm$^2$ and in an extreme case, the adhesion strength to the dentine is close to 200 kg/cm$^2$. This unexpected effect is mainly attained by combining ascorbic acid or a derivative thereof with the above-mentioned specific monomer and filler. Use of ascorbic acid or a derivative thereof for improving the adhesion strength is first proposed by the present invention. In other words, the finding that a high improvement of the adhesion strength is attained by combining ascorbic acid or a derivative thereof with the acidic group-containing monomer and filler is quite surprising. As is apparent from the foregoing description, ascorbic acid or its derivative is a very important constituent component in the adhesive composition of the present invention.

The kind of ascorbic acid or its derivative is not particularly critical in the present invention, and known compounds can be used. As preferred examples of the ascorbic acid there can be mentioned L-ascorbic acid, D-iso-ascorbic acid and dehydroascorbic acid, and as preferred examples of the ascorbic acid derivative, there can be mentioned metal salts of ascorbic acid, such as sodium L-ascorbate, calcium L-ascorbate and sodium D-iso-ascorbate, and ascorbic acid esters such as stearyl L-ascorbate, palmityl L-ascorbate and 2,6-dipalmityl L-ascorbate. In order to obtain an adhesive composition having an especially high adhesion strength, L-ascorbic acid or an alkali metal salt or ascorbic acid, for example, sodium L-ascorbate or sodium D-iso-ascorbate, is especially preferably used.

In the present invention, the amount used of ascorbic acid and/or its derivative is not particularly critical, and it is sufficient if the component (d) is used in an amount of 0.01 to 10 parts by weight, preferably 0.05 to 5 parts by weight, per 100 parts by weight of the monomer mixture.

In the adhesive composition of the present invention, it is preferred that a small amount of a polymerization inhibitor such as hydroquinone, hydroquinone monomethyl ether or butylhydroxytoluene be incorporated according to need in addition to the above-mentioned components (a) through (d).

In the present invention, incorporation of an inorganic filler often produces preferred results according to the kind of an adherend. For example, if an inorganic filler is added, the mechanical strength and water resistance are improved, and the flowability and coating property can be adjusted.

In the present invention, an organic solvent can be added according to need. Easily volatilizable organic solvents such as acetone, methylene chloride, chloroform and ethanol are preferred. The amount added of the organic solvent is appropriately selected according to the intended use. For example, the organic solvent is used in an amount of 1 to 200 parts by weight per 100 parts by weight of the monomer mixture.

In the case where the adhesive composition of the present invention is applied to the dentine, it is preferred that the surface of the dentine be subjected to an ordinary pretreatment such as acid etching. As the acid etchant, there can be ordinary used an aqueous solution of phosphoric acid or a calcium, iron, copper, nickel, zinc or manganese salt of hydrochloric acid, sulfuric acid or an organic acid, or an aqueous solution of a mixture of a salt as mentioned above and an inorganic acid such as phosphoric acid or an organic acid such as citric acid, malic acid or tartaric acid. For the adhesive composition of the present invention, the latter aqueous solution of the mixture is preferable. An aqueous solution of ferric chloride/citric acid, an aqueous solution of ferric chloride/phosphoric acid, an aqueous solution of ferric citrate and an aqueous solution of zinc chloride/citric acid are especially preferred.

In general, the adhesive composition of the present invention is handled and stored in a two-pack system. Namely, liquid components and powder components are independently filled in two different packs, and at the curing and bonding step, necessary amounts of the liquid and powder components are taken out from the packs and they are kneaded together. For example, there is generally adopted a method in which the monomer components and the organic peroxide (or one of the tertiary amine and the α-diketone) are filled as the liquid component in one pack and the filler, ascorbic acid (or its derivative) and the organic peroxide (or one of the tertiary amine and α-diketone) are filled as the powder component in another pack. Of course, the liquid component and/or the powder component can be further divided into different packs. Moreover, the liquid and powder components can be packed into small packs for one application.

As is apparent from the foregoing description, in the adhesive composition of the present invention, the adhesion strength and durability are highly improved. The adhesive composition shows an especially excellent effect when applied to a hard tissue of the human body, such as a bone or tooth, particularly the dentine, bonding of which is difficult according to the conventional technique.

Furthermore, the adhesive composition is effective for bonding of metals, ceramics and organic polymers.

The present invention will now be described in detail with reference to the following examples that by no means limit the scope of the invention.

Incidentally, in the following examples and comparative examples, the adhesion strength to the dentine and the adhesion strength to a metal were determined according to the following procedures. (a) Adhesion Strength to Dentine A foretooth was extracted in a bovine within 24 hours from the point of slaughter, and under pouring of water, the bottom surface of the tooth was polished by emery paper #800 so that the dentine was horizontally exposed. A double-coated tape having a hole having a diameter of 4 mm was applied to the surface of the exposed dentine.

The liquid component of the adhesive component was coated on the hole by a small brush, and equal amounts of the newly collected liquid component and the powder component were mixed together and the surface of the dentine was bonded to the section of an acrylic resin rod having a diameter of 8 mm through the mixture. The mixture was exposed to a visible light source for 30 seconds, when it contained the α-diketone as a polymerization initiator. After passage of 1 hour, the bovine tooth having the acrylic resin rod bonded thereto was immersed in water at 37° C. for 24 hours. The bovine tooth was taken out from water, and the adhesion strength between the dentine and the adhesive composition was measured by a tensile tester (crosshead speed: 10 mm/min). (b) Adhesion Strength to Metal A fresh metal surface was exposed by emery paper #800 and the surface was coarsened by an alumina sandblast treatment. A double-coated having a diameter of 4 mm was applied to the metal surface. The liquid component of the adhesive composition was coated on the hole by a small brush, and a mixture of equal amounts of the newly collected liquid component and the powder component was applied to the hole and the metal surface was bonded to the section of a stainless steel rod (which had been subjected to an alumina sandblast treatment in advance). The adhesion strength was measured in the same manner as described in (a) above.

EXAMPLES 1 THROUGH 9

Adhesive compositions were prepared according to the following recipe, and the adhesion strength to the dentine was measured.

| Liquid Component | |
|---|---|
| Vinyl monomer shown in Table 1 | (100 − x) parts by weight |
| Acidic group-containing vinyl monomer shown in Table 1 | x parts by weight |
| Ethyl 4-(N,N-dimethylamino) benzoate | 1.5 parts by weight |
| Powder Component | |
| Polymethyl methacrylate | 24 parts by weight |
| Methyl methacrylate/ethyl methacrylate copolymer | 76 parts by weight |
| Silica powder | 0.1 part by weight |
| Dibenzoyl peroxide | 1.5 parts by weight |
| Sodium L-ascorbate | 3.0 parts by weight |

In Example 9 as a comparative example, the acidic group-containing vinyl monomer was not added in the composition of Example 1 but 20 parts by weight of methyl methacrylate was further added instead.

The data of the adhesion strength obtained in each of the foregoing examples are shown in Table 1.

Incidentally, before the bonding treatment, the dentine surface was contacted with an aqueous solution containing 3% of ferric chloride and 10% of citric acid for 60 seconds and was then washed with water and dried with air.

TABLE 1

| Example No. | Acidic Group-Containing Vinyl Monomer (parts by weight) | Vinyl Monomer (parts by weight) | Adhesion Strength (kg/cm$^2$) |
|---|---|---|---|
| 1 | 11-methacryloxy-1,1-undecanedicarboxylic acid (20) | methyl methacrylate (80) | 173 |
| 2 | 11-methacryloxy-1,1-undecanedicarboxylic acid (10) | methyl methacrylate (90) | 147 |
| 3 | 13-methacryloxy-1,1-tridecanedicarboxylic acid (20) | methyl methacrylate (80) | 142 |
| 4 | 7-methacryloxy-1,1-heptanedicarboxylic acid (20) | methyl methacrylate (80) | 135 |
| 5 | 4-methacryloxyethyl-trimellitic anhydride (10) | methyl methacrylate (90) | 118 |
| 6 | 11-methacryloxy-1,1-undecanedicarboxylic acid (20) | bisphenol A diglycidyl methacrylate (40), 2-hydroxyethyl methacrylate (16), tri-ethylene glycol dimethacrylate (24) | 141 |
| 7 | 11-methacryloxy-1,1-undercanedicarboxylic acid (5) | methyl methacrylate (95) | 129 |
| 8 | 11-methyacryloxy-1,1-undercanedicarboxylic acid (2.5) | methyl methacrylate (97.5) | 110 |
| 9 | — | methyl methacrylate (100) | 14 |

EXAMPLES 10 THROUGH 18

Adhesion compositions were prepared in the same manner as described in Example 1 except that the kinds and amounts of the tertiary amine and organic peroxide were charged as shown in Table 2, and the adhesion strength to the dentine was measured. The obtained results are shown in Table 2.

TABLE 2

| Example No. | Organic Peroxide (parts by weight) | Tertiary Amine (parts by weight) | Adhesion Strength (kg/cm$^2$) |
|---|---|---|---|
| 10 | dibenzoyl peroxide (1.5) | ethyl 4-(N,N-dimethylamino)benzoate (1.5) | 173 |
| 11 | diacyl peroxide (0.8) | ethyl 4-(N,N-dimethylamino)benzoate (1.5) | 157 |
| 12 | dilauroyl peroxide (1.5) | ethyl 4-(N,N-dimethylamino)benzoate (1.5) | 149 |
| 13 | dibenzoyl peroxide (1.5) | ethyl 4-(N,N-dimethylamino)benzoate (0.5) | 153 |
| 14 | dibenzoyl peroxide (1.5) | isoamyl 4-(N,N-dimethylamino)benzoate (1.5) | 162 |
| 15 | dibenzoyl peroxide (1.5) | 4-(N,N-diethylamino) benzaldehyde (1.5) | 110 |
| 16 | dibenzoyl peroxide (1.5) | N,N-dimethyl-p-toluidine (1.5) | 122 |
| 17 | dibenzoyl peroxide (1.0) | N,N-dimethyl-p-toluidine (1.5) | 154 |
| 18 | dibenzoyl peroxide (0.5) | N,N-dimethyl-p-toluidine (1.5) | 132 |
| 19 | dibenzoyl peroxide (1.5) | N,N-di($\beta$-hydroxyethyl)-p-toluidine (1.5) | 117 |
| 20 | dibenzoyl peroxide (1.5) | N,N-dimethyl-m-anisidine (1.5) | 105 |

EXAMPLES 21 THROUGH 25 AND COMPARATIVE EXAMPLES 1 THROUGH 4

Adhesive compositions were prepared in the same manner as described in Example 1 except that a compound shown in Table 3 was used in an amount shown in Table 3 instead of sodium L-ascorbate, and the adhesion strength to the dentine was measured. The obtained results are shown in Table 3.

For comparison, the ascorbic acid or its derivative was not added, or other organic acid or organic acid salt was added instead of the ascorbic acid or its salt. Also the measurement results obtained in these comparative examples are shown in Table 3.

TABLE 3

| Example No. | Ascorbic Acid or Its Derivative | Amount Added (parts by weight) | Adhesion Strength (k/cm$^2$) |
|---|---|---|---|
| 21 | L-ascorbic acid | 2 | 123 |
| 22 | D-iso-ascorbic acid | 1 | 124 |
| 23 | dehydroascorbic acid | 3 | 151 |
| 24 | sodium D-ascorbate | 1 | 186 |
| 25 | stearyl L-ascorbate | 3 | 112 |
| Comparative Example No. | | | |
| 1 | DL-malic acid | 3 | 25 |
| 2 | potassium benzoate | 3 | 42 |
| 3 | sodium p-toluene-sulfinate | 3 | 61 |
| 4 | not added | — | 40 |

EXAMPLES 26 THROUGH 37

Adhesion compositions were prepared according to the following recipe, and after the preliminary treatment was carried out in the same manner as described in Example 1, the adhesion strength was measured. The obtained results are shown in Table 4.

| Liquid Component | |
|---|---|
| Methyl methacrylate | amount shown in Table 4 |
| Acidic group-containing vinyl monomer shown in Table 4 | amount shown in Table 4 |
| Acidic group-containing vinyl monomer shown in Table 4 | amount shown in Table 4 |
| Organic peroxide shown in Table 4 | amount shown in Table 4 |
| Powder Component | |
| Polymethylmethacrylate | 24 parts by weight |
| Methyl methacrylate/ethyl methacrylate copolymer | 76 parts by weight |
| silica powder | 0.1 part by weight |
| Ascorbic acid or its derivative | amount shown in Table 4 |

TABLE 4

| Example No. | Acidic Group-Containing Vinyl Monomer (parts by weight) | Vinyl Monomer (parts by weight) | Organic Peroxide (parts by weight) | Ascorbic Acid or Derivative (parts by weight) | Adhesion Strength (kg/cm$^2$) |
|---|---|---|---|---|---|
| 26 | 11-methacryloxy-1,1-undecane-dicarboxylic acid (20) | methyl methacrylate (80) | dibenzoyl peroxide (1.5) | sodium L-ascorbate (3.0) | 122 |
| 27 | 11-methacryloxy-1,1-undecane-dicarboxylic acid (10) | methyl methacrylate (90) | dibenzoyl peroxide (1.5) | sodium L-ascorbate (3.0) | 108 |
| 28 | 13-methacryloxy-1,1-tridecane-dicarboxylic acid (20) | methyl methacrylate (80) | dibenzoyl peroxide (1.5) | sodium L-ascorbate (3.0) | 96 |
| 29 | 7-methacryloxy-1,1-heptane-dicarboxylic acid (20) | methyl methacrylate (80) | dibenzoyl peroxide (1.5) | sodium L-ascorbate (3.0) | 93 |
| 30 | 4-methacryloxyethyltrimellitic acid (10) | methyl methacrylate (90) | dibenzoyl peroxide (1.5) | sodium L-ascorbate (3.0) | 90 |
| 31 | 11-methacryloxy-1,1-undecane-dicarboxylic acid (20) | methyl methacrylate (80) | dilauroyl peroxide (1.0) | sodium L-ascorbate (3.0) | 118 |
| 32 | 11-methacryloxy-1,1-unedecane-dicarboxylic acid (20) | methyl methacrylate (80) | diacyl peroxide (1.5) | sodium L-ascorbate (3.0) | 115 |
| 33 | 11-methacryloxy-1,1-undecane-dicarboxylic acid (20) | methyl methacrylate (80) | dibenzoyl peroxide (1.5) | L-ascorbic acid (3.0) | 93 |
| 34 | 11-methacryloxy-1,1-undecane-dicarboxylic acid (20) | methyl methacrylate (80) | dibenzoyl peroxide (1.5) | D-iso-ascorbic acid (2.0) | 90 |
| 35 | 11-methacryloxy-1,1-undecane-dicarboxylic acid (20) | methyl methacrylate (80) | dibenzoyl peroxide (1.5) | dihydroascorbic acid (2.0) | 105 |
| 36 | 11-methacryloxy-1,1-undecane-dicarboxylic acid (20) | methyl methacrylate (80) | dibenzoyl peroxide (1.5) | sodium D-iso-ascorbate (2.0) | 127 |
| 37 | 11-methacryloxy-1,1-undecane-dicarboxylic acid (20) | methyl methacrylate (80) | dibenzoyl peroxide (1.5) | stearyl L-ascorbate (3.0) | 95 |

EXAMPLES 38 THROUGH 48

Adhesive compositions were prepared according to the following recipe, and the preliminary treatment was carried out in the same manner as described in Example 1 and the adhesion strength to the dentine was measured. The obtained results are shown in Table 5.

Liquid Component
Methyl methacrylate — amount shown in Table 5
Acidic group-containing vinyl monomer shown in Table 5 — amount shown in Table 5
Tertiary amine shown in Table 5 — amount shown in Table 5

Powder Component
Polymethyl methacrylate — 24 parts by weight
Methyl methacrylate/ethyl methacrylate copolymer — 76 parts by weight
Silica powder — 0.1 part by weight
Ascorbic acid or its derivative — amount shown in Table 5

TABLE 5

| Example No. | Acidic Group-Containing Vinyl Monomer (parts by weight) | Vinyl Monomer (parts by weight) | Tertiary Amine (parts by weight) | Ascorbic Acid or Its Derivative (parts by weight) | Adhesion Strength (kg/cm$^2$) |
|---|---|---|---|---|---|
| 38 | 11-methacryloxy-1,1-undecane-dicarboxylic acid (20) | methyl methacrylate (80) | ethyl 4-(N,N-dimethylamino)-benzoate (1.5) | sodium L-ascorbate (3.0) | 108 |
| 39 | 11-methacryloxy-1,1-undecane-dicarboxylic acid (10) | methyl methacrylate (90) | ethyl 4-(N,N-dimethylamino)-benzoate (1.5) | sodium L-ascorbate (3.0) | 93 |
| 40 | 13-methacryloxy-1,1-tridecane-dicarboxylic acid (20) | methyl methacrylate (80) | ethyl 4-(N,N-dimethylamino)-benzoate (1.5) | sodium L-ascorbate (3.0) | 91 |
| 41 | 7-methacryloxy-1,1-heptane-dicarboxylic acid (20) | methyl methacrylate (80) | ethyl 4-(N,N-dimethylamino)-benzoate (1.5) | sodium L-ascorbate (3.0) | 87 |
| 42 | 4-methacryloxyethyltrimellitic acid (10) | methyl methacrylate (80) | ethyl 4-(N,N-dimethylamino)-benzoate (1.5) | sodium L-ascorbate (3.0) | 85 |
| 43 | 11-methacryloxy-1,1-undecane-dicarboxylic acid (20) | methyl methacrylate (80) | isoamyl 4-(N,N-dimethylamino)-benzoate (1.0) | sodium L-ascorbate (3.0) | 106 |
| 44 | 11-methacryloxy-1,1-undecane-dicarboxylic acid (20) | methyl methacrylate (80) | ethyl 4-(N,N-dimethylamino)-benzoate (1.0) | L-ascorbic acide (3.0) | 103 |
| 45 | 11-methacryloxy-1,1-undecane-dicarboxylic acid (20) | methyl methacrylate (80) | ethyl 4-(N,N-dimethylamino)-benzoate (1.5) | D-iso-ascorbic acid (2.0) | 101 |
| 46 | 11-methacryloxy-1,1-undecane-dicarboxylic acid (20) | methyl methacrylate (80) | ethyl 4-(N,N-dimethylamino)-benzoate (1.5) | dehydroascorbic acid (3.0) | 110 |
| 47 | 11-methacryloxy-1,1-undecane-dicarboxylic acid (20) | methyl methacrylate (80) | ethyl 4-(N,N-dimethylamino)-benzoate (1.5) | sodium D-iso-ascorbate (2.0) | 108 |
| 48 | 11-methacryloxy-1,1-undecane-dicarboxylic acid (20) | methyl methacrylate (80) | ethyl 4-(N,N-dimethylamino)- | stearyl L-ascorbate (3.0) | 93 |

TABLE 5-continued

| Example No. | Acidic Group-Containing Vinyl Monomer (parts by weight) | Vinyl Monomer (parts by weight) | Tertiary Amine (parts by weight) | Ascorbic Acid or Its Derivative (parts by weight) | Adhesion Strength (kg/cm$^2$) |
|---|---|---|---|---|---|
| | | | | benzoate (1.5) | |

EXAMPLES 49 THROUGH 55

The adhesion strength to the dentine of the adhesion composition of Example 1 was measured in the same manner as described in Example 1 except that a pretreatment agent shown in Table 6 was used instead of the aqueous solution containing 3% of ferric chloride and 10% of citric acid, used in Example 1. The obtained results are shown in Table 6.

TABLE 6

| Example No. | Pretreatment Agent | Adhesion Strength (kg/cm$^2$) |
|---|---|---|
| 49 | aqueous solution containing 10% of phosphoric acid | 108 |
| 50 | aqueous solution containing 3% of ferric chloride and 10% of phosphoric acid | 187 |
| 51 | aqueous solution containing 10% of ferric citrate | 153 |
| 52 | aqueous solution containing 3% of ferric sulfate and 10% of citric acid | 130 |
| 53 | aqueous solution containing 3% of zinc chloride and 10% of citric acid | 192 |
| 54 | aqueous solution containing 3% of manganess chloride and 10% of citric acid | 90 |
| 55 | aqueous solution containing 3% of calcium chloride and 10% citric acid | 109 |

EXAMPLES 56 AND 57 COMPARATIVE EXAMPLES 5 THROUGH 8

Adhesive compositions shown in Table 7 were prepared and the adhesion strengths to sandblasted metal surfaces were measured. The obtained results are shown in Table 7.

TABLE 7

| | Adhesion Composition | | | Adhesion Strength (kg/cm$^2$) |
|---|---|---|---|---|
| | Liquid Componet (parts by weight) | Powder Component (parts by weight) | Adherend Methyl | |
| Example 56 | 11-methacryloxy-1,1-undecanedicarboxylic acid (5), methyl methacrylate (95) N,N-dimethyl-p-toluidine (1.5) | polymethyl methacrylate (24), methyl methacrylate/ethyl methacrylate co-polymer (76), silica powder (1.0), dibenzoyl peroxide (1.0), L-ascorbic acid (3.0) | nickel-chromium alloy | 350 |
| Example 57 | 11-methacryloxy-1,1-undecanedicarboxylic acid (5), methyl methacrylate (95) N,N-dimethyl-p-toluidine (1.5) | polymethyl methacrylate (24), methyl methacrylate/ethyl methacrylate co-polymer (76), silica powder (1.0), dibenzoyl peroxide (1.0), L-ascorbic acid (3.0) | cobalt chromium alloy | 390 |
| Comparative Example 5 | methyl methacrylate (100), N,N-dimethyl-p-toluidine (1.5) | polymethyl methacrylate (24), methyl methacrylate/ethyl methacrylate co-polymer (76), silica powder (1.0), dibenzoyl peroxide (1.0), L-ascorbic acid (3.0) | nickel-chromium alloy | 160 |
| Comparative Example 6 | methyl methacrylate (100), N,N-dimethyl-p-toluidine (1.5) | polymethyl methacrylate (24), methyl methacrylate/ethyl methacrylate co-polymer (76), silica powder (1.0), dibenzoyl peroxide (1.0), L-ascorbic acid (3.0) | cobalt-chromium alloy | 152 |
| Comparative Example 7 | 11-methacryloxy-1,1-undecanedicarboxylic acid (5), | polymethyl methacrylate (24), methyl methacrylate/ethyl metha- | nickel-chromium alloy | 145 |

TABLE 7-continued

| | Adhesion Composition | | | Adhesion |
|---|---|---|---|---|
| | Liquid Componet (parts by weight) | Powder Component (parts by weight) | Adherend Methyl | Strength (kg/cm$^2$) |
| Comparative Example 8 | methyl methacrylate (95), N,N-dimethyl-p-toluidine (1.5)<br><br>11-methacryloxy-1,1-undecanedicarboxylic acid (5), methyl methacrylate (95), N,N-dimethyl-p-toluidine (1.5) | crylate copolymer (76), silica powder (0.1) debenzoyl peroxide (1.0), sodium p-toluenesulfinate (3.0)<br>polymethyl methacrylate (24), methyl methacrylate/ethyl methacrylate copolymer (76), silica powder (0.1) debenzoyl peroxide (1.0), sodium p-toluenesulfinate (3.0) | cobalt-chromium alloy | 104 |

EXAMPLES 58 THROUGH 62

Adhesive composition were prepared according to the following recipe, and the adhesion strength to the dentine was prepared in the same manner as described in Example 1. The obtained results are shown in Table 8.

| | |
|---|---|
| Liquid Component | |
| 11-Methacryloxy-1,1-undecanedicarboxylic acid | 10 parts by weight |
| Methyl metacrylate | 90 parts by weight |
| N,N-Dimethyl-p-toluidine | 1.5 parts by weight |
| Powder Component | |
| Organic filler shown in Table 8 | (100 − x) parts by weight |
| Inorganic filler shown in Table 8 | x parts by weight |
| Dibenzoyl peroxide | 1.5 parts by weight |
| L-Asorbic acid | 3.0 parts by weight |

TABLE 8

| Example No. | Organic Filler (parts by weight) | Inorganic Filler (parts by weight) | Adhesion Strength (kg/cm$^2$) |
|---|---|---|---|
| 58 | methyl methacrylate/ethyl methycrylate copolymer (70) | silica-zirconia (30) | 128 |
| 59 | methyl methacrylate/ethyl methacrylate copolymer (50) | silica-zirconia (50) | 109 |
| 60 | methyl methacrylate/ethyl methacrylate copolymer (70) | quartz (30) | 123 |
| 61 | methyl methacrylate (90) | hydroxyapatite (10) | 110 |
| 62 | methyl methacrylate (80) | silica-titania (20) | 105 |

EXAMPLE 63 AND COMPARATIVE EXAMPLE 9

The dentine of a bovine tooth as described in Example 1 was exposed, and a paraffin wax having a hole having a diameter of 4 mm was fixed to the exposed surface by using a double-coated tape to form an imitation cavity having the exposed surface as the bottom surface.

A mixture of equal amounts of components A and B of an adhesive composition shown in Table 9 was coated on said bottom surface, and a commercially available photocurable composite resin (Palfique lite supplied by Tokuyama Soda) was inserted in the immitation cavity. Then, the composite resin was irradiated for 30 seconds by using a commercially available visible ray irradiator (White Light supplied by Takara Bermont) to cure the composite resin.

After curing of the composite resin, the paraffin wax was removed, and the bovine tooth/cured composite resin bonded structure was immersed in water at 37° C. for 24 hours. A metal attachment was set to each of the cured composite resin and the bovine tooth, and the adhesion strength was measured by a tensile tester (cross-head speed=10 mm/min).

Incidentally, instead of the polymethyl methacrylate filler used in Example 63, the same amount of methyl methacrylate monomer was used.

The obtained results are shown in Table 9.

TABLE 9

| | Component A (parts by weight) | Component B (parts by weight) | Adhesion Strength (kg/cm$^2$) |
|---|---|---|---|
| Example 63 | 11-methacryloxy-1,1-undecanedicarboxylic acid (20), methyl methacrylate (80), N,N-dimethyl-p-toluidine (1.5) | polymethylmethacrylate (100), silica powder (0.1), dibenzoyl peroxide (1.5), L-asorbic acid (3.0) | 110 |
| Comparative Example | 11-methacryloxy-1,1-undecanedicarboxylic acid (20), methyl methacrylate (80), N,N-dimethyl-p-toluidine (1.5) | methyl methacrylate (100), dibenzoyl peroxide (1.5), L-asorbic acid (3.0) | 30 |

EXAMPLES 64 THROUGH 69 AND COMPARATIVE EXAMPLE 10

Adhesion composition were prepared according to the following recipe, and after the preliminary treatment was carried out in the same manner as described in Example 1, the adhesion strength was measured. The obtained results are shown in Table 10.

| | parts by weight |
|---|---|
| Liquid Component | (100 − x) |
| Vinyl monomer shown in Table 10 | |
| Acidic group-comtaining vinyl monomer shown in Table 10 | x |
| camphorquinone | 0.4 |
| Powder Component | |

-continued

| | parts by weight |
|---|---|
| Polymethyl methacrylate | 24 |
| Methyl methacrylate/ethyl methacrylate copolymer | 76 |
| Silica powder | 0.1 |
| Dibenzoyl peroxide | 1.5 |
| Sodium L-ascorbate | 3.0 |

TABLE 10

| Example No. | Acidic Group-Containing Vinyl Monomer (parts by weight) | Vinyl Monomer (parts by weight) | Adhesion Strength (kg/cm$^2$) |
|---|---|---|---|
| 64 | 11-methacryloxy-1,1-undecanedicarboxylic acid (20) | methyl methacrylate (80) | 108 |
| 65 | 11-methacryloxy-1,1-undecanedicarboxylic acid (10) | methyl methacrylate (90) | 98 |
| 66 | 13-methacryloxy-1,1-tridecanedicarboxylic acid (20) | methyl methacrylate (80) | 104 |
| 67 | 7-methacryloxy-1,1-heptanedicarboxylic acid (20) | methyl methacrylate (80) | 102 |
| 68 | 4-methacryloxyethyltrimellic acid anhydride (10) | methyl methacrylate (90) | 101 |
| 69 | 11-methacryloxy-1,1-undecanedicarboxlic acid (20) | bisphenol A diglycidyl methacrylate (40) 2-hydroxyethyl methacrylate (16) triethylene glycol dimethacrylate (24) | 106 |
| Comparative Example 10 | | methyl methacrylate (100) | 14 |

EXAMPLES 70 THROUGH 76 AND COMPARATIVE EXAMPLES 11 THROUGH 14

Adhesion compositions were prepared in the same manner as described in Example 1 except that the kinds and amounts of α-diketone and ascorbic acid or its derivative were changed as shown in Table 11, and the adhesion strength to the dentine was measured. The obtained results are shown in Table 11.

TABLE 11

| Example No. | α-diketone (parts by weight) | Asorbic acid or its derivative (parts by weight) | Adhesion Strength (kg/cm$^2$) |
|---|---|---|---|
| 70 | benzil (1.0) | sodium L-ascorbate (3.0) | 100 |
| 71 | diacetyl (0.5) | sodium L-ascorbate (3.0) | 98 |
| 72 | camphorquinone (0.4) | L-ascorbic acid (3.0) | 92 |
| 73 | camphorquinone (0.4) | D-iso-ascorbic acid (1.0) | 90 |
| 74 | camphorquinone (0.4) | dehydroascorbic acid (3.0) | 90 |
| 75 | camphorquinone (0.4) | sodium D-iso-ascorbate (1.0) | 109 |
| 76 | camphorquinone (0.4) | stearyl L-ascorbate (3.0) | 93 |
| Comparative Example | | | |
| 11 | camphorquinone (0.4) | DL-malic acid (3.0) | 24 |
| 12 | camphorquinone (0.4) | potassium benzoate (3.0) | 38 |
| 13 | camphorquinone (0.4) | sodium p-toulene sulfinate (3.0) | 27 |
| 14 | camphorquionone (0.4) | not added (—) | 20 |

EXAMPLE 77 AND COMPARATIVE EXAMPLE 15

A mixture of equal amounts of components A and B of an adhesive compositions shown in Table 12 were prepared, and after the preliminary treatment was carried out in the same manner as described in Example 63, the adhesion strength was measured. The obtained results are shown in Table 12.

TABLE 12

| | Component A (parts by weight) | Component B (parts by weight) | Adhesive Strength (kg/cm$^2$) |
|---|---|---|---|
| Example 77 | 11-methacryloxy-undecanedicarboxylic acid (20) methyl methacrylate (80) camphorquinone (0.4) | polymethyl methacrylate (100) silica powder (0.1) dibenzoyl peroxide L-ascorbic acid (3.0) | 120 |
| Comparative Example 15 | 11-methacryloxy-undecanedicarboxylic acid (20) methyl methacrylate (80) camphorquinone (0.4) | methyl methacrylate (100) dibenzoyl peroxide (1.5) L-ascorbic acid (3.0) | 41 |

We claim:

1. An adhesive composition comprising (a) 100 parts by weight of a monomer mixture comprising a vinyl monomer having an acidic group in the molecule represented by the following formula:

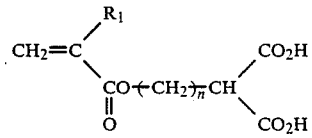

wherein R$_1$ stands for a hydrogen atom or a methyl group, and n is a number of from 4 to 12, and a vinyl monomer copolymerizable with said vinyl monomer, (b) 10 to 500 parts by weight of a filler, (c) 0.01 to 10 parts by weight of a polymerization initiator and (d) 0.01 to 100 parts by weight of ascorbic acid or a derivative thereof.

2. An adhesive composition comprising (a) 100 parts by weight of a monomer mixture comprising a vinyl monomer having an acidic group in the molecule represented by the following formula:

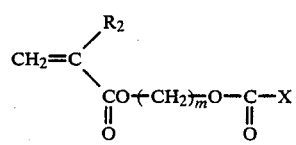

wherein $R_2$ stands for a hydrogen atom or a methyl group, m is a number of from 2 to 4, and X stands for

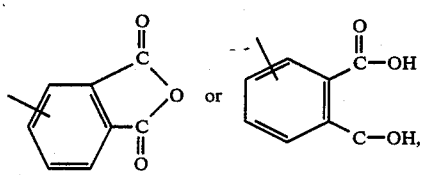

and a vinyl monomer copolymerizable with said vinyl monomer, (b) 10 to 500 parts by weight of a filler, (c) 0.01 to 10 parts by weight of a polymerization initiator and (d) 0.01 to 10 parts by weight of ascorbic acid or a derivative thereof.

3. An adhesive resin composition of a two-pack system comprising (i) a liquid component comprising a vinyl monomer having an acidic group in the molecule, which is selected from the group consisting of a monomer represented by the following formula:

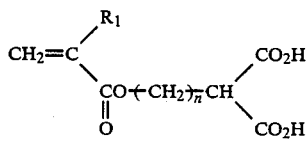

wherein $R_1$ stands for a hydrogen atom or a methyl group, and n is a number of from 4 to 12, and a monomer represented by the following formula:

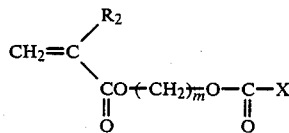

wherein $R_2$ stands for a hydrogen atom or a methyl group, m is a number of from 2 to 4, and X stands for

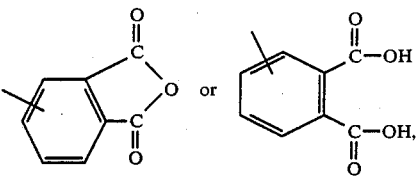

or a monomer mixture of said acidic group-containing vinyl monomer and a vinyl monomer copolymerizable therewith and (ii) a powder component comprising ascorbic acid or a derivative thereof and a filler, wherein the components (i) and (ii) are filled in different packs and, at the time of curing, appropriate amounts of the liquid and powder components are taken out from the packs and are mixed.

4. An adhesive composition as set forth in claim 1 or 2, wherein the content of the vinyl monomer having an acidic group in the monomer mixture is 1 to 90% by weight.

5. An adhesive composition as set forth in claim 1 or 2, wherein the copolymerizable vinyl monomer is an acrylic acid ester or a methacrylic acid ester.

6. An adhesive composition as set forth in claim 1 or 2, wherein the filler is a homopolymer or copolymer of an acrylic acid ester or a methacrylic acid ester.

7. An adhesive composition as set forth in claim 1 or 2, wherein the polymerization initiator is at least one member selected from the group consisting of organic peroxides and tertiary amines.

8. An adhesive composition as set forth in claim 6, wherein the organic peroxide is a diacyl peroxide.

9. An adhesive composition as set forth in claim 4, wherein the content of the vinyl monomer having an acidic group in the monomer mixture is 1 to 50% by weight.

10. An adhesive composition as set forth in claim 1 or 2, wherein said filler has a particle size of 0.01 to 500 μm.

11. An adhesive composition as set forth in claim 10, wherein said filler has a particle size of 0.01 to 200 μm.

12. An adhesive composition as set forth in claim 1 or 2, wherein said polymerization initiator comprises a mixture of an organic peroxide and a tertiary amine.

13. An adhesive composition as set forth in claim 1 or 2, wherein said polymerization initiator comprises a mixture of an organic peroxide and an α-diketone.

14. An adhesive composition as set forth in claim 1 or 2, wherein said ascorbic acid is selected from the group consisting of L-ascorbic acid, D-iso-ascorbic acid and dehydroascorbic acid.

15. An adhesive composition as set forth in claim 1 or 2, wherein said ascorbic acid derivative is selected from the group consisting of metal salts thereof and esters thereof.

* * * * *

UNITED STATES PATENT AND TRADEMARK OFFICE
CERTIFICATE OF CORRECTION

PATENT NO. : 4,918,136

DATED : April 17, 1990

INVENTOR(S) : TOSHIO KAWAGUCHI, ET AL.

It is certified that error appears in the above-identified patent and that said Letters Patent is hereby corrected as shown below:

On the title page, add the Foreign Application Priority Data as follows:

```
--March 28, 1988......[JP].............63-72050
  May    6, 1988......[JP]............63-109156--.
```

Signed and Sealed this

Seventeenth Day of March, 1992

Attest:

HARRY F. MANBECK, JR.

*Attesting Officer*  *Commissioner of Patents and Trademarks*